United States Patent [19]

Anderson

[11] Patent Number: 5,026,352
[45] Date of Patent: Jun. 25, 1991

[54] ADJUSTABLE FITMENTS FOR MEDICAL TUBES

[75] Inventor: Gregor J. M. Anderson, Folkestone, England

[73] Assignee: Smiths Industries Public Limited Company, London, England

[21] Appl. No.: 455,101

[22] Filed: Dec. 22, 1989

[30] Foreign Application Priority Data

Feb. 3, 1989 [GB] United Kingdom ............... 8902459

[51] Int. Cl.⁵ ............................................ A61M 16/00
[52] U.S. Cl. ..................................... 604/178; 604/174; 128/DIG. 26; 128/207.17
[58] Field of Search ..................... 604/174, 178, 179; 128/DIG. 26, 207.14, 207.17

[56] References Cited

U.S. PATENT DOCUMENTS

| 4,249,529 | 2/1981 | Nestor et al. | 128/207.17 |
| 4,449,527 | 5/1984 | Hinton | 128/207.17 |
| 4,498,903 | 2/1985 | Mathew | 604/179 |
| 4,530,354 | 7/1985 | Froilan | 128/207.17 |
| 4,649,913 | 3/1987 | Watson | 604/174 |
| 4,683,882 | 8/1987 | Laird | 604/179 |
| 4,774,944 | 10/1988 | Mischiwski | 128/207.17 |

FOREIGN PATENT DOCUMENTS 8002645 12/1980 PCT Int'l Appl. .
8403217 8/1984 PCT Int'l Appl. .

Primary Examiner—Stephen C. Pellegrino
Assistant Examiner—Ralph A. Lewis
Attorney, Agent, or Firm—Pollock, Vande Sande and Priddy

[57] ABSTRACT

An adjustable flange for a tracheostomy tube has a circular aperture and two semi-circular arms hinged with one another by an integral flexible web. One arm has a smooth surface that is slidable along the tube; and the other arm has circumferential ribs that bite into the surface of the tube. A bolt passes through one arm and into a threaded recess of the other enabling the flange to be locked in position.

8 Claims, 1 Drawing Sheet

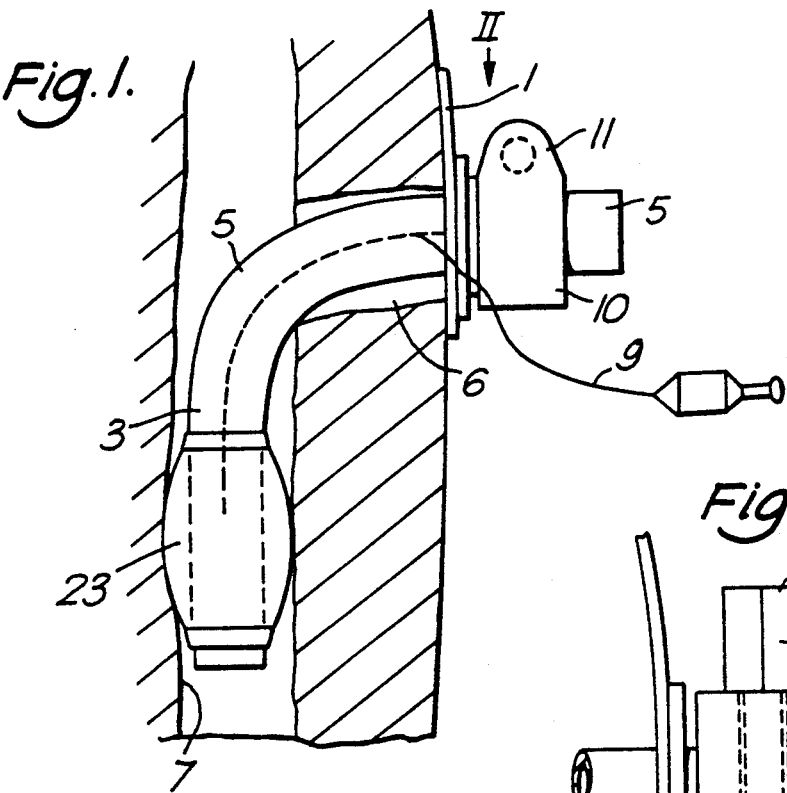
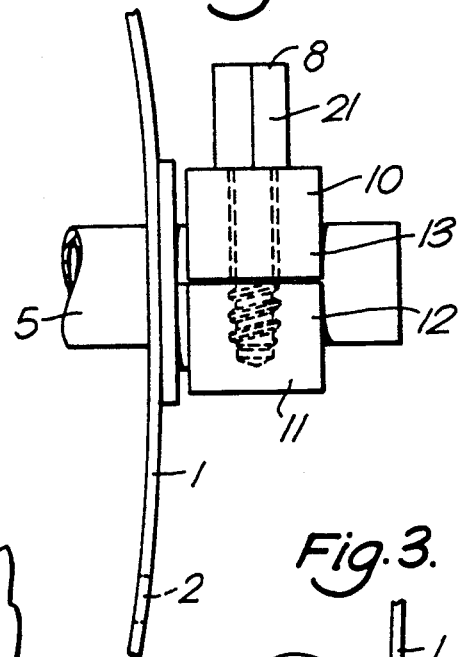
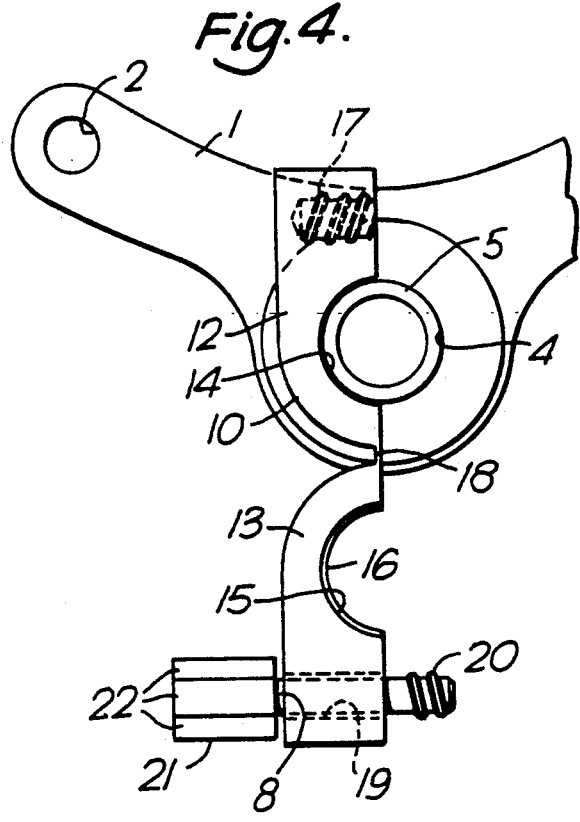
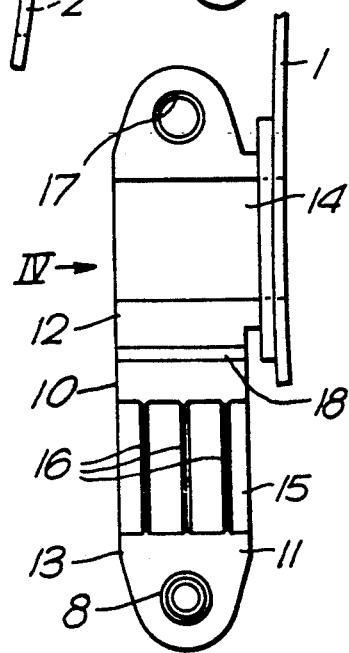

ADJUSTABLE FITMENTS FOR MEDICAL TUBES

BACKGROUND OF THE INVENTION

This invention relates to adjustable fitments for medical tubes.

The invention is more specifically concerned with adjustable flanges for tracheal tubes.

Tracheostomy tubes are inserted into the trachea of a patient through a surgically made opening, or stoma, in the patient's neck to provide an airway or a path for gas ventilation.

In order to stabilize the tube and limit the extent of insertion, the tube is provided with a flange near its machine end that is arranged to be located close to the surface of the patient s neck. The flange is usually provided with a slot or the like by which a strap passing round the patient's neck can be fixed to the flange. Although generally a range of tubes are available of different sizes, for patients of different builds, there is nevertheless significant variation in the thickness of tissue between the neck surface and the trachea. This leads to possible problems of undue pressure on the rear surface of the trachea if the flange is located away from the surface of the patient's neck, or compression of tissue in the region of the stoma if the flange is located too close to the patient end of the tube.

Various proposals have been made to prevent this problem, such as by use of a flange that is adjustable along the length of the tube. These adjustable flanges, however, have not been entirely satisfactory because of their complexity, cost, difficulties of use, or difficulties of providing a secure mounting to the surface of a smooth tube which may be wet and slippery.

BRIEF SUMMARY OF THE INVENTION

It is an object of the present invention to provide an adjustable fitment for a medical tube that can be used to alleviate these difficulties.

According to one aspect of the present invention there is provided an adjustable fitment for a medical tube including an integral polymeric moulding having first and second substantially rigid arms linked by an integral hinge member, said first and second arms each having a region of substantially semi-circular section adapted to embrace a portion of said tube, one of said arms having a threaded recess therein located to align with a mounting aperture through the other of said arms, and a locking bolt rotatably received in said mounting aperture and adapted to extend therethrough, said locking bolt having a threaded end which engages in said threaded recess so that the two arms can be tightened about the tube to lock the fitment in position by means of the locking bolt.

The semi-circular region recess of at least one of said arms is preferably provided with a surface formation shaped to bite into the surface of the tube so as to improve the grip of the fitment on the tube. The surface formation may take the form of one or more circumferential ribs.

According to another aspect of the present invention there is provided a medical tube assembly including a fitment according to the above one aspect of the present invention. The medical tube assembly may be a tracheostomy tube assembly.

A tracheostomy tube assembly including an adjustable flange, in accordance with the present invention, will now be described, by way of example, with reference to the accompanying drawings.

BRIEF DESCRIPTION OF THE DRAWINGS

FIG. 1 is a side elevation view of the tracheostomy tube assembly in use;

FIG. 2 is plan view of the assembly of FIG. 1 along the arrow II;

FIG. 3 is a plan enlarged view of the flange in an open state; and

FIG. 4 is an end view of the flange in an open state along the arrow IV of FIG. 3.

DETAILED DESCRIPTION OF PREFERRED EMBODIMENT

The flange comprises a flexible plate 1 of plastic material provided with an opening 2 at each end, for receiving a securing tape (not shown), and a central, circular aperture 4 for receiving the machine end of a tracheostomy tube 5. Secured to the flange plate 1 is a releasable locking device 10 which enables the flange to be slid along the tube to the desired location in contact with the surface of the patient's neck and locked in that position.

The tracheostomy tube 5 is of conventional construction and is made of a deformable, resilient plastics material such as PVC with a circular section. The machine end of the tube 5 is straight and, in use, emerges from a surgically made stoma 6 between the patient's neck surface and trachea 7. The machine end of the tube 5 is uninterrupted apart from the adjustable flange, although a coupling may be joined to the machine end of the tube.

A cuff 23 embraces the tube 5 close to its patient end. The cuff 23 is inflated, in use, to seal with the trachea 7, by means of an inflation lumen 3 extending along the tube within its wall which connects with an inflation line 9 close to the machine end of the tube.

The locking device 10 comprises an integral moulding 11 of nylon, or a similar polymeric material, and a locking bolt 8, also of nylon. The moulding 11 has two rigid arms 12 and 13 each of which have a region 14 and 15, formed on one surface, of semi-circular section. The upper arm 12 (as seen in FIG. 3) is attached to the plate 1 so that its semi-circular region 14 is aligned with the aperture 4 through the plate. The region 14 of this arm 12 has a smooth surface which slides easily along the tube 5 when unlocked. The smooth surface of the arm 12 overlies the inflation lumen 3 so that there is less risk of occluding the lumen when the device 10 is tightened about the tube 5.

The outer end of the arm 12 has a circular recess 17 which is threaded. The inner end of the arm 12 is connected with the other arm 13 by means by an integral, flexible web 18 which provides a hinge between the two arms.

The other arm 13 is similar in shape but its semi-circular region 15 has surface formations in the form of three circumferential ribs 16. These ribs 16 bite into the surface of the tube 5 when the device 10 is locked about the tube. The outer end of the arm 13 has an aperture 19 therethrough in which the locking bolt 8 is retained. One end 20 of the bolt 8 is threaded to mate with the recess 17, the other end 21 being shaped to enable it to be gripped between the finger and thumb, such as by means of flats 22. When the arm 13 is closed about the tube 5, the aperture 19 aligns with the threaded recess 17 in the other arm so that the bolt 8 can be screwed into the recess.

In use, the patient end of the tube 5 is inserted in the trachea 7 through the stoma 6 in the usual way. The adjustable flange is then slid along the machine end of the tube with the arms 12 and 13 open or in a loosely closed state. When the plate 2 abuts the surface of the patient's neck, the arms can be locked tightly about the tube by screwing the bolt 8 firmly into the recess 17. The flange and the tube 5 may both carry markings which are aligned when the flange is at the correct angular orientation relative to the tube, so as to ensure that the tube is not twisted to one side in the trachea.

The locking device 10 enables the flange to be easily positioned to provide maximum comfort to the patient whilst also securely retaining the tube. The simple construction of the flange enables it to be made accurately at low cost.

It will be appreciated that the locking device could be used to provide adjustable fitments for medical tubes other than flanges for tracheostomy tubes.

What I claim is:

1. An adjustable fitment for a medical tube comprising: a flange having a circular aperture, an integral polymeric moulding secured to said flange and having first and second substantially rigid arms, an integral hinge member linking said rigid arms, said first and second arms each having a region of semi-circular section, the semi-circular region in one of said arms being aligned with said circular aperture, said semi-circular sections being shaped to embrace a portion of said tube, one of said arms having a threaded recess therein, the other arm having a mounting aperture therethrough which is aligned with aid threaded recess in said one arm; and a locking bolt rotatably received in said mounting aperture and extending therethrough, said locking bolt having a threaded end which engages in said threaded recess so that the two arms can be tightened about the tube to lock the fitment in position by means of the locking bolt.

2. An adjustable fitment according to claim 1 wherein the semi-circular region of the other of said arms has a surface formation shaped to bit into the surface of said tube.

3. An adjustable fitment according to claim 2, wherein said surface formation includes at least one circumferential rib.

4. An adjustable fitment according to claim 1, wherein the semi-circular region of said one arm has a smooth surface, a said smooth surface being slidable along the tube.

5. An adjustable fitment according to claim 1, wherein aid integral hinge is a flexible web.

6. An adjustable fitment for a medical tube, comprising: an integral polymeric moulding, said moulding having first and second substnatially rigid arms and an integral hinge member, said hinge member linking said rigid arms, wherein said first and second arms each having a region of semi-circular section, said semi-circular sections being shaped to embrace a portion of said tube, the semi-circular section of the first arm being smooth so that it is slidable along the tube, the semi-circular section of the second arm having a plurality of surface formations that bite into the surface of the tube, one of the said arms having a threaded recess therein, and the other arm having a mounting aperture therethrough which is aligned with said threaded recess in said one arm; a locking bolt, said locking bolt being rotatably received in said mounting aperture and extending therethrough, and said locking bolt having a threaded en which engages in said threaded recess so that the two arms can be tightened about the tube to lock the fitment in position; and a flange having a circular aperture, said flange being mounted on said moulding with said circulator aperture being in alignment with the semi-circular region of the first arm.

7. A medical tube assembly comprising a tube and an adjustable fitment on the tube, said tube having an inflation curb and an inflation lumen, said inflation lumen extending along he tube and opening into the cuff, said fitment comprising an integral polymeric moulding having first and second substnatially rigid arms and an integral hinge member, said hinge member linking said rigid arms, said first and second arms each having a region of semi-circular section shaped to embrace a portion of said tube, one of said arms having a threaded recess therein, the other arm having a mounting aperture therethrough which can be aligned with aid threaded recess in said one arm by movement of said arms relative to one another about said hinge member, and a locking bolt rotatably received in said mounting aperture and extending therethrough,. said locking bolt having a threaded end which engages in said threaded recess so that the two arms can be tightened about the tube to lock the fitment in position, and of the arms of the fitment having a surface formation shaped to bit into the surface of said tube, and the other of the arms being smooth so that the fitment can be slid along he tube when the two arms are not tightened about the tube, the smooth arm being located to overlie said lumen so that the tightening of the two arms does not occlude the lumen.

8. A medical tube assembly according to claim 7, wherein said tube is a tracheostomy tube.

* * * * *